United States Patent [19]

Hatschek

[11] 4,429,699
[45] Feb. 7, 1984

[54] BLOOD PRESSURE MEASURING EQUIPMENT

[75] Inventor: Rudolf A. Hatschek, Fribourg, Switzerland

[73] Assignee: Asulab AG, Biel, Switzerland

[21] Appl. No.: 235,561

[22] Filed: Feb. 12, 1981

[30] Foreign Application Priority Data

Feb. 18, 1980 [CH] Switzerland .......................... 1299/80

[51] Int. Cl.$^3$ ............................................. A61F 00/00
[52] U.S. Cl. ..................................... 128/681; 128/686
[58] Field of Search ................................ 128/680–683, 128/686, 677–679

[56] References Cited

U.S. PATENT DOCUMENTS

| | | | |
|---|---|---|---|
| 3,371,661 | 3/1968 | Budde | 128/680 |
| 3,765,405 | 10/1973 | Natkanski | 128/686 |
| 3,812,844 | 5/1974 | Sokol | 128/686 |

FOREIGN PATENT DOCUMENTS 1906346 8/1970 Fed. Rep. of Germany ...... 128/686
7502303 8/1976 Netherlands ...................... 128/686

*Primary Examiner*—Kyle L. Howell
*Assistant Examiner*—John E. Hanley
*Attorney, Agent, or Firm*—Michael J. Striker

[57] ABSTRACT

There is disclosed blood pressure measuring equipment comprising a sleeve with a chamber inflatable by fluid and a measurement transducer for determining the circumference of an arm to which the sleeve is attached. A pressure sensor is provided to detect pressure in the chamber and is electrically connected through electronic components with two analog stores for storage of measured pressure values representing systolic and diastolic blood pressure. An indicating control device is connected between the stores and a digital display unit and comprises a pressure value correcting device by means of which the pressure values can be corrected, in dependence on the circumference of the arm as determined by the transducer, during readout of the stores. As a result, errors in the pressure values due to different arm circumferences can be eliminated.

9 Claims, 7 Drawing Figures

Fig. 7

BLOOD PRESSURE MEASURING EQUIPMENT

BACKGROUND OF THE INVENTION

The present invention relates to blood pressure measuring equipment.

Blood pressure measuring equipment described in U.S. Pat. No. 3,450,131 comprises a sleeve which is attachable to the arm of a person and which defines an inflatable deformable chamber, a microphone being housed in the sleeve. The chamber is coupled to a pressure sensor which is connected via an analog-digital converter, which can be switched on and off, and a gate circuit with a pressure recording device. The microphone is connected through an amplifier with a logic circuit.

During blood pressure measurement, the sleeve is inflated to a pressure lying above systolic pressure and then slowly vented. In that case, Korotkoff tones are generated in a certain pressure range and converted by the microphone into electrical signals. On the occurrence of each Korotkoff tone signal, the analog-digital converter and the gate circuit are controlled by the logic circuit in such a manner that the instantaneous pressure measured by the pressure sensor is recorded in the pressure recording device. The first recorded pressure value corresponds to systolic pressure and the last recorded pressure value to diastolic pressure.

It is known from the "Handbuch der inneren Medizin", published by G. von Bergman, W. Frey and H. Schwiegk, Vol. 9, "Herz und Kreislauf", 5th Part, 1960, Springer Verlag, and "Arterielle Hochdruckerkrankungen", 1970, by A Sturm Jr. Dr. Dietrich Steinkopff Verlag, that the measured pressure values can include an error depending on the circumference of the arm. Such errors are dependent on the ratio of the width of the sleeve to the circumference of the arm.

According to the two afore-mentioned reference works, the errors in in question could be eliminated if the circumference of the arm is measured and then either a narrower or wider sleeve attached to the arm according to its circumference, or else a measured pressure value corrected in dependence on the measured circumference by means of a previously determined correction table or formula.

These correction methods have the disadvantage that the person carrying out the blood pressure measurement must determine the circumference of the arm by a separate measurement and then either select and attach one of several available sleeves or else subsequently perform a correcting calculation. These methods are thus time-consuming as well as complicated, and therefore not suitable in practice.

OBJECT OF THE INVENTION

The invention has as its principal object the provision of blood pressure measuring equipment in which different circumferences of arms or other members to which a measuring sleeve is attached do not give rise to measurement errors, such errors being avoidable without the person performing the measurement having to carry out additional correction operations.

Other objects and advantages of the invention will be apparent from the following description.

SUMMARY OF THE INVENTION

According to the present invention there is provided blood pressure measuring equipment comprising a sleeve attachable to a limb of a person, the sleeve defining a chamber which is inflatable by fluid and being provided with a measurement transducer for measuring the circumference or diameter of a limb, such as an arm, to which the sleeve is attached. A pressure sensor is provided for detecting fluid pressure in said chamber, and a pressure value determining circuit is electrically connected to the sensor to determine values of detected pressure levels in the chamber. The pressure value determining circuit includes pressure value correcting means connected to the transducer and adapted to correct at least some of the determined pressure values, for example values defined as representing systolic and diastolic blood pressure measurements, in dependence on the limb circumference or diameter measurement determined by the transducer.

For clarification, it is noted that the references in the following description and claims to blood pressure and air chamber pressure are to be understood as denoting excess pressure measured with respect to ambient air pressure.

BRIEF DESCRIPTION OF THE DRAWINGS

An embodiment of the present invention will now be more particularly described by way of example and with reference to the accompanying drawings, in which.

DESCRIPTION OF THE PREFERRED EMBODIMENT

Figure 1:
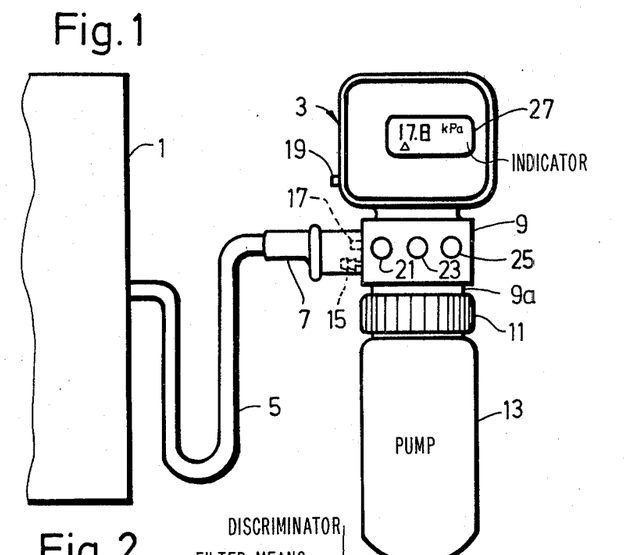
FIG. 1 is a schematic plan view of blood pressure measuring equipment according to the said embodiment.

Referring now to the accompanying drawings, in FIG. 1 there is shown blood pressure measuring equipment comprising a sleeve or cuff 1 attachable to the arm of a person to be examined and an appliance indicated generally by 3. The sleeve 1 comprises a rubber bag defining a deformable and inflatable air chamber and is equipped with a microphone and a measurement transducer for determination of the circumference of the person's arm. The sleeve 1 is detachably connected to the appliance 3 by a line 5, which comprises an air hose connected to the air chamber and a cable connected to the microphone and the transducer, the line being provided at the appliance end with a coupling socket 7. The appliance 3 comprises a housing 9 provided with a threaded shank 9a to which a pump 13 with a substantially cylindrical rubber pump bulb is detachably fastened by means of a box nut 11. An air hose connection nipple 15 and an electrical connection pin 17, formed by a chassis plug, are provided on the housing 9 for coupling thereto of the socket 7. A connection element 19, also formed by a chassis plug, is included for the connection of a headphone. The appliance 3 also comprises three nonlocking pushbutton switches 21, 23 and 25, a three-place digital liquid crystal indicating unit 27 and various pneumatic and electronic components, as will be subsequently described, accommodated in the interior of the housing 9.

Figure 2:
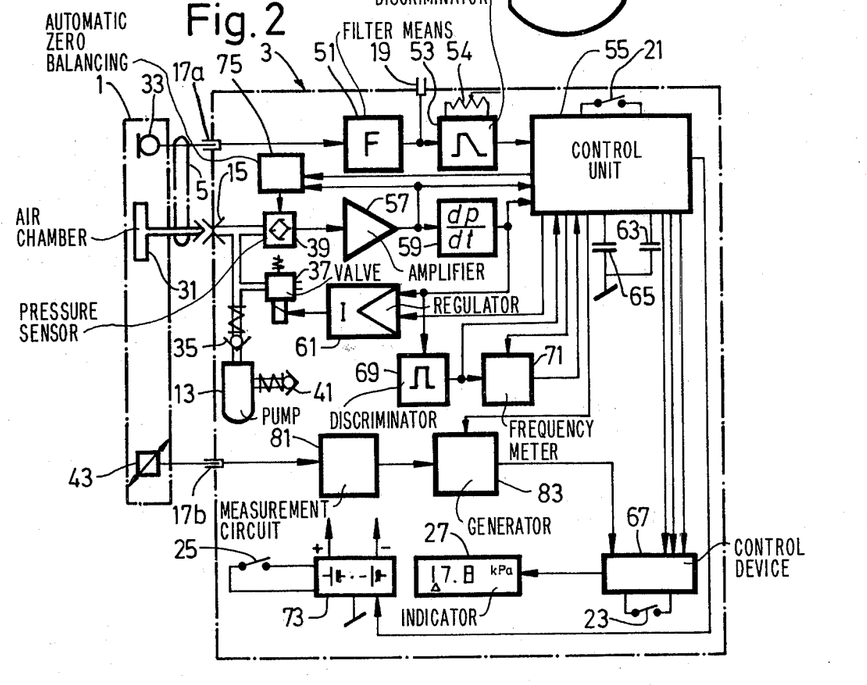
FIG. 2 is a schematic block diagram of the equipment of FIG. 1.

FIG. 2 shows the inflatable air chamber, referenced 31, the microphone, referenced 33, and the measurement transducer, referenced 43, of the sleeve 1 as well as some of the pneumatic and electronic components in the appliance 3. The air chamber 31 is connected by the air hose in the line 5, and by air lines in the appliance 3, via a check valve 35 with the pump 13, an electrically controllable vent valve 37 and a pressure sensor 39. The pump 13 is provided with an air inlet having a check valve 41. The two check valves 35 and 41 are so arranged that by alternating manual compression and release of the pump bulb 13 air can be sucked from the ambient atmosphere and pumped into the air chamber 31.

The microphone 33 is connected by electrical conductors through a part 17a of the connection pin 17 with the input of a filter means 51, the output of which is connected with the headphone connection element 19 and with a discriminator 53, which comprises a trimming potentiometer 54 for setting of a lower threshold value and a pulse shaper. The output of the pulse shaper is connected to a control unit 55.

The pressure sensor 39 comprises a measurement converter bridge circuit formed by piezo-resistive elements and is connected with the input of an amplifier 57, the output of which is connected via a differentiator 59, and via a parallel connection bridging the differentiator, with the control unit 55. The control unit 55 and the amplifier 57 are also connected at outputs thereof with a device 75 for automatic zero balancing, the output of the device 75 being connected to the pressure sensor 39. The output of the differentiator 59 is also connected to the control unit 55 and additionally to an input of a regulator 61. The control unit 55 is connected to another input of the regulator 61, the output of which is connected with an electromagnetic actuating means of the vent valve 37. The control unit 55 additionally has two connections which are connected to, respectively, two analog memories 63 and 65 each formed by a respective capacitor. Three outputs of the control unit 55 are connected to three inputs of an indicating control device 67 which includes, amongst other things, an analog-digital converter and which in turn is connected to the indicating unit 27.

A discriminator 69 is connected at its input to the output of the differentiator 59, and at its output to an input of a heartbeat frequency meter 71 and an input of the control unit 55. The meter 71 is connected at a control input thereof to an output of the control unit 55 and comprises an analog memory connected at an output to an input of the control unit 55. The switch 21 is connected to the control unit 55 and the switch 23 to the indicating control device 67. Also present is a voltage source 73, which includes a battery and which is connected to supply voltage connections of the different operative components and to an earth connection. The switch 25 and also the control unit 55 are connected to the voltage source 73, which, apart from the battery, comprises logic elements and a regulator for stabilisation of the supply voltage. The battery is accommodated in a battery compartment closable by a lid.

The measurement transducer 43 is connected through lines and a part 17b of the connection pin 17 with a measurement circuit 81, the output of which is connected with an input of a correction value generator 83. The generator 83 also has a control input connected with an output of the control unit 55. The output of the generator 83 is connected with a control input of the indicating control device 67.

Figures 3, 4:
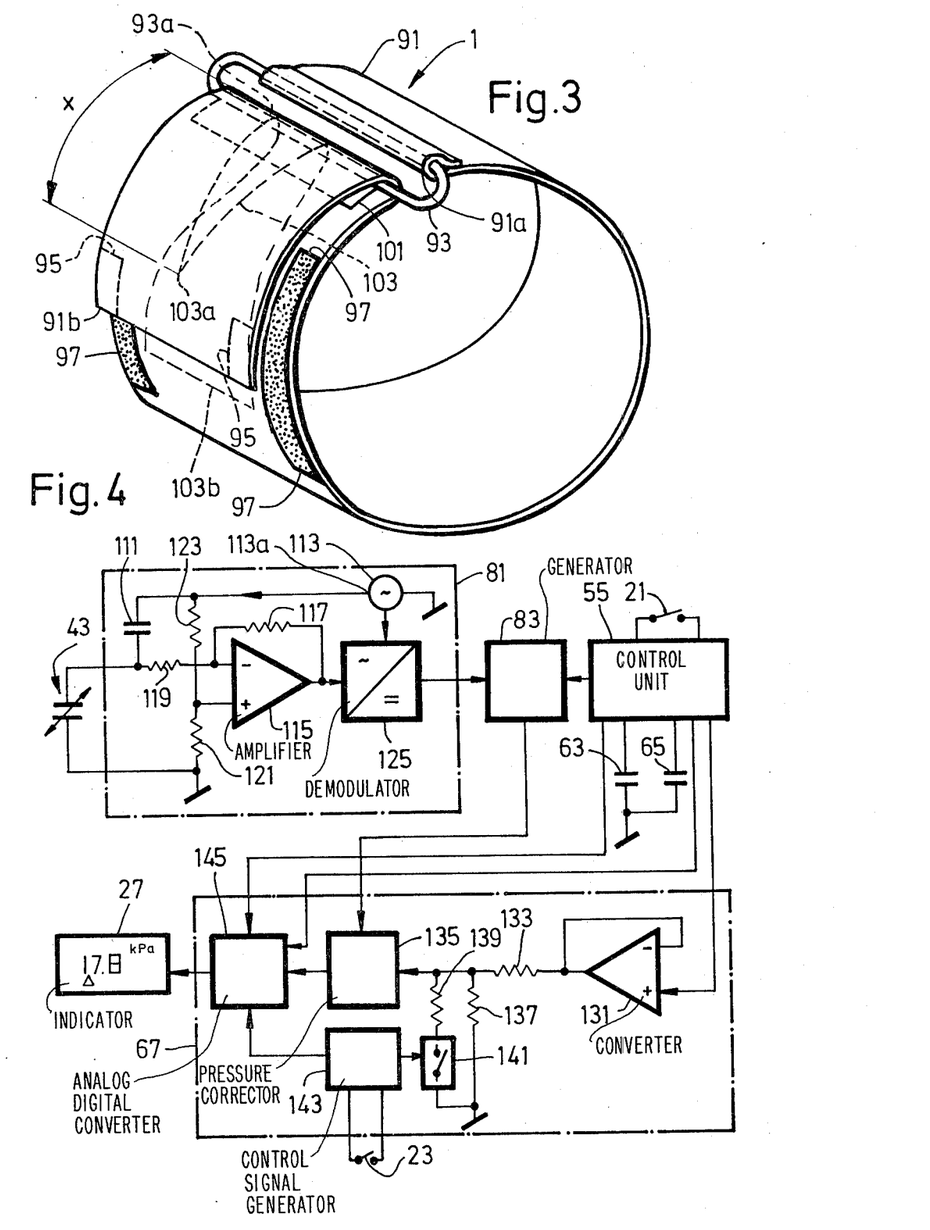
FIG. 3 is a perspective view of a sleeve, with a capacitive measurement transducer, in the equipment of FIG. 1.
FIG. 4 is a circuit diagram of the capacitive measurement transducer and associated electronic components serving for correction of pressure measurement values.

The sleeve 1, illustrated separately in simplified form in FIG. 3, comprises a band 91 with two ends 91a and 91b. A buckle 93 of electrically insulating plastics material and forming an elongate ring is attached to the end 91a. The band 91 either contains or defines the deformable and inflatable air chamber 31, which is provided by the interior of an elongate bag. The microphone 33 (not shown in FIG. 3) is attached to the band 91.

For carrying out a blood pressure measurement, the sleeve 1 is laid around an arm of the person to be examined. The band 91b is then pulled through the buckle 93, as illustrated in FIG. 3, and folded over the bar 93a of the buckle remote from the end 91a. The end 91b is provided with attachment elements 95 at the edge regions of its side which is disposed outwardly before the folding over. The band portion overlapped by the folded-over band end section is provided with strip-shaped attachment elements 97 extending along the band edges. The attachment elements 95 and 97 consist of fabric pieces with interconnectable hooks and eyes and together form a Velcro-type closure by which the folded-over band end section can be detachably fastened to the overlapped band portion by pressing thereagainst.

The measurement transducer 43 is constructed as a capacitive measurement transducer and comprises two electrodes 101 and 103. The electrode 101 consists of an uninsulated, electrically highly conductive metal blank attached to the buckle part 93a, the dimension of the electrode in the longitudinal direction of the band being at most about two centimeters. The electrode 101 can be pivotably attached or rigidly attached in a predetermined position to the buckle bar 93a, and/or possibly be of a flexible construction. The electrode 103 is formed by a thin flexible plastics material film with a metallic layer at one side. The electrode 103 is attached to that side of the band 91 and the inflatable air chamber 31 which, in the band portion enclosing the arm, is remote from the arm. The plastics film, which serves as electrical insulation of the electrode 103, faces outwardly of the band 91, so that when the band 91 is folded over the buckle bar 93a the plastics film material forms the dielectric separating the two electrodes of the transducer 43. The electrode 103 is substantially larger than the electrode 101 in the length direction of the band 91 and extends over at least 20% of the entire band length. The electrode 103 has the shape of a sharply pointed isosceles triangle, the base of which extends at right angles to the length direction of the band. The electrode end 103a formed by the apex of the triangle is disposed in the proximity of the band end 91b, while the electrode end 103b formed by the base of the triangle is disposed at some distance from the band end 91b. The width of the electrode 103 measured at right angles to the length direction of the band thus varies along the band and progressively increases in the direction away from the band end 91b. The width of the electrode 101 measured transversely to the length direction of the band is at least equal to the maximum width of the electrode 103.

The two electrodes 101 and 103 are connected with the connecting part 17b through a multicore cable (not shown in FIG. 3) which can contain the conductors for the microphone 33, these conductors being connected to the connection pin 17a.

When the sleeve is attached to the arm of a person with the band end section folded over the buckle bar 93a, the electrode 101, and the two portions of the electrode 103 facing the electrode 101 from different sides, together form the capacitor of the transducer 43. If the capacitance of this capacitor is designated by C and the spacing of the centre line of the two above-mentioned portions of the electrode 103 from the electrode end 103a by x, then the relationship applies:

$$x = C/C_o \qquad (1),$$

wherein $C_o$ is a constant. The circumference U of the arm is then given by the relationship:

$$U = L - x \qquad (2),$$

wherein L is a length which is predetermined by the construction of the sleeve 1. The length L is equal to the spacing of the electrode end 103a from the band end 91a measured with the sleeve unwound plus the distance of the buckle bar 93a from the band end 91a. The arm circumference U can thus be determined through measurement of the capacitance C.

As can be seen from FIG. 4, one of the electrodes of the capacitive measurement transducer 43 is connected with earth in the measurement circuit 81 and the other electrode through a capacitor 111 with an output 113a of a low frequency generator 113. A differential operational amplifier 115, provided with a feedback coupling through a resistor 117, has an inverting input which is connected through a resistor 119 with the transducer 43 and the capacitor 111. The amplifier 115 also has a non-inverting input which is connected via a resistor 121 with earth and via a resistor 123 with the output 113a of the generator 113. The output of the amplifier 115 is connected with one input of a demodulator 125. The demodulator has a control input which is connected with a further output of the generator 113. A further connection of the generator 113 is connected with earth. The output of the demodulator 125 forms the output of the measurement circuit 81 and is connected with the correction value generator 83. The measurement circuit 81 and/or the correction value generator 83 is or are provided with manually settable setting means (not shown) for balancing and calibrating of the circumference-measuring channel.

The indicating control device 67 comprises an impedance converter 131 formed by an amplifier with full feedback. An output of the control unit 55 is connected with the non-inverting input of the impedance converter 131 through a connection which serves for transmission of analog signals representing measured pressure values. The output of the impedance converter 131 is connected through a resistor 133 with the input of a pressure value correcter 135. This input of the pressure correcter 135 is also connected via a resistor 137 with earth and via a resistor 139, which is connected in parallel with the resistor 137, with an electronic or electromagnetic switching device 141 connected in series. The control input of the switching device 141, which in the case of an electromagnetic switching device is formed by the coil connection thereof, is connected with the output of a control signal generator 143, which in turn is connected with the switch 23. The output of the pressure value corrector 135 is connected with one input of an analog-digital converter 145. The control signal generator 143 also has an output connected with one input of the analog-digital converter 145, the output of which is connected with the digital liquid crystal indicating unit 27. The output of the correction value generator 83 is connected with one input of the pressure value correcter 135. Two different outputs of the control unit 55 are connected through separate connections with the analog-digital converter 145. One of these connections serves for the transmission of signals having magnitudes representing heart frequency and the other for the transmission of the signals which characterise the value (continuously measured blood pressure, systolic pressure, diastolic pressure, heart frequency) to be indicated. The analog-digital converter 145 also comprises a decoder for control of the liquid crystal numeral indication and for control of the units and symbols to be indicated.

Figure 5:
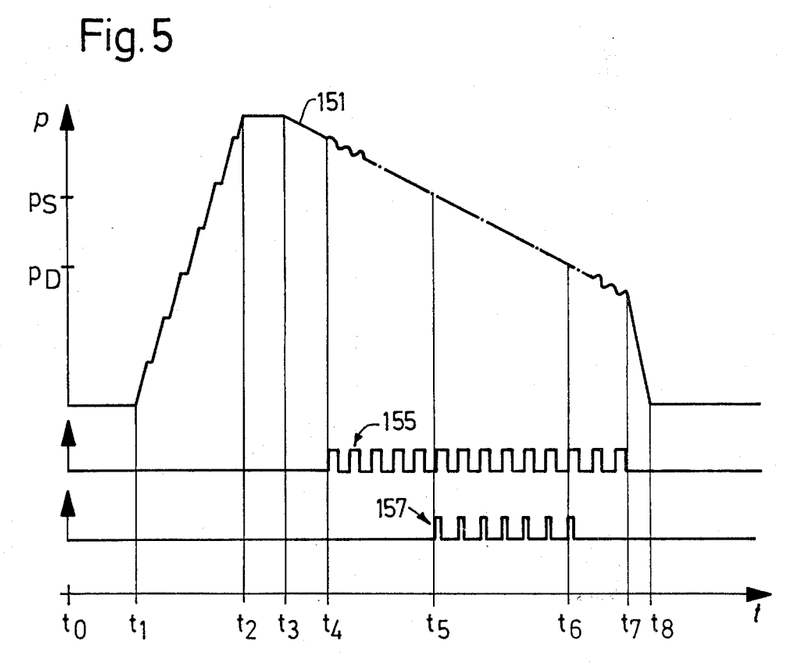
FIG. 5 is a diagram illustrating the temporal course of a blood pressure measurement by the equipment.

The operation of the blood pressure measuring equipment shall now be explained in detail with reference to the diagram of FIG. 5.

For performance of a measurement, the sleeve 1 is connected by the line 5 with the appliance 3 and is attached to the arm of the person to be examined. The dimensions of the appliance are such that it can conveniently be held by one hand, for which purpose the pump 13 also serves as handgrip.

The change in the pressure p in the air chamber 31 in the course of the time t will be discussed first. The temporal course of the pressure p is represented by the curve 151 of the diagram of FIG. 5. The pressure sensor 39 during measurement generates a voltage which is proportional to the pressure p.

When the sleeve is attached, the appliance is made operationally ready at the instant $t_0$ through a brief depression of the ON/OFF switch 25. The valve 37 is fully open at this instant and in the time interval from the instant $t_0$ to the instant $t_1$. During this time interval, the pressure sensor 39 is automatically balanced to zero by the zero balance device 75. The end of this balancing, at the instant $t_1$, is signalled by the indicating unit 27 indicating the value zero.

The control unit 55 is so constructed that it connects the output of the amplifier 57 with the impedance converter 131 of the indicating control device 67 at regular time intervals of, for example, 0.3 seconds from the zero balancing to the end of the measurement. The indicating unit 27 indicates the instantaneous pressure on each occasion.

After the automatic zero balancing, air is pumped into the air chamber 31 through manual actuation of the pump 13. When the pressure has risen to a magnitude, sufficiently above the likely systolic pressure $p_s$, the pumping process is terminated at the instant $t_2$. Shortly after termination of the inflation process, air starts to flow at the instant $t_3$ out of the air chamber 31 through the valve 37 and into the environment, so that the pressure in the air chamber falls. In that case, the differential quotient dp/dt is determined by the differentiator 59. The regulator 61 regulates the outflow valve 37 in such a manner that the differential quotient dp/dt remains constant during the actual measurement phase apart from pressure fluctuations, which are caused by heart activity and which will be further explained.

When the pressure p is now reduced from its maximum pressure lying above the systolic pressure $p_s$, the pressure fluctuations caused by heartbeats occur from the instant $t_4$. These pressure fluctuations are detected by the differentiator 59. The discriminator 69 then generates a pulse on each pressure fluctuation generated by a heartbeat for which the differential quotient $dp/dt$ exceeds a predetermined threshold value of at least 100 Pascals per second, for example 400 Pascals per second. This pulse sequence is designated by 155 in FIG. 5.

When the pressure in the air chamber 31 is reduced to be in a certain range, blood flowing through the artery enclosed by the sleeve 1 generates noises, the so-called Korotkoff tones, on each blood stroke generated by a heartbeat. These Korotkoff tones are converted by the microphone 3 into electrical tone frequency signals and transmitted through the filter means 51, which preferably also amplifies the signals to the discriminator 53. When the voltages of the Korotkoff tone signals exceed the lower threshold value determined by the discriminator 53, the pulse shaper of the discriminator feeds a respective pulse to the control unit 55. This pulse sequence is designated by 157 in FIG. 5 and extends from the instant $t_5$ to the instant $t_6$.

In the control unit, the pulse generated through the pressure fluctuations and the pulses generated through the Korotkoff tones are fed to an AND-gate. The AND-gate forms a coincidence circuit and opens a window for the pulses of the pulse sequence 157 during each pulse of the pulse sequence 155. Signals from the microphone are thus further processed only when they fall into a window opened by a pressure fluctuation, i.e. when a coincidence exists between the tone signals and the pressure fluctuations. As a result, the Korotkoff tones can be distinguished from interfering noises and the latter be suppressed.

The control unit 55 includes an electronic switching device which connects the output of the amplifier 57 with the memory 63 when the appliance is switched on.

The control unit 55 also includes means to ascertain the appearance of the first Korotkoff signal passing the afore-mentioned AND-gate. When the first Korotkoff signal arrives, the line from the amplifier 57 of the pressure-measuring channel is separated from the memory 63. The memory 63 accordingly stores the pressure value present on the arrival of the first Korotkoff tone signal, i.e. the systolic pressure.

As the pressure in the air chamber 31 drops, further Korotkoff tones follow the first Korotkoff tone. The control unit 55 comprises means which briefly connects the output of the amplifier 57 with the memory 65 on each Korotkoff tone, i.e. on each pulse of the pulse sequence 125. A new pressure value is thus stored in the memory 65 on each Korotkoff tone, these pressure values progressively reducing. As already mentioned, the pulse sequence 157 extends to the instant $t_6$. As no further pulses occur after the instant $t_6$, the value of the pressure p measured at the instant $t_6$ remains stored in the memory 65 until the appliance is switched off. This storage value then represents the diastolic pressure.

The control unit 55 also comprises circuit means by which it can be ascertained when no further Korotkoff tone has occurred during a predetermined time interval of 2 to 10, for example 5, seconds. At the end of this time interval, namely at the instant $t_7$, the control unit 55 delivers to the regulator 61 a signal which has the effect that the valve 37 is fully opened. The pressure p then drops very rapidly and at the instant $t_8$ is again at the value zero, i.e. the ambient air pressure.

The control unit also sets the heartbeat frequency meter 71 into operation temporarily so that this measures the heartbeat during the occurrence of the pulse sequence 123 and determines the mean value thereof. This is stored in the memory of the meter 71 until the appliance is switched off.

The nature of the control unit 55 is also that the memory 63, the store 65 or the memory of the meter 71 can be cyclically interrogated by a brief depression of the switch 21. The relevant storage value stored in analog form is then fed to the indicating control device 67 and converted by this into a digital signal. This is fed to the indicating unit 27 so that the unit thus selectably indicates systolic or diastolic pressure or heartbeat frequency. The value being indicated is identified by the indicating unit through display of a symbol, namely a triangle with an upwardly directed point, a triangle with a downwardly directed point, or the letter p.

When all three storage values have been read off, the appliance 3 can be switched off by a brief depression of the ON/OFF switch 25, whereby the measurement is concluded.

Now that the general mode of operation of the equipment has been explained, some individual features will be described in connection with the pressure measurement. The pressure can be indicated selectably in kilopascals or torrs, both during the continuous pressure indication in the course of the actual measurement procedure and during read-out of the stores. The switch over from kilopascals to torrs and vice versa is effected by briefly depressing the switch 23. Pressing of the switch 23 has the effect that the control signal generator 143 opens or closes the switching device 141. The analog signal, which is fed by the impedance converter 131 to the pressure value correcter 135 and which represents a measured pressure, is differently attenuated by the resistance network consisting of the resistors 133, 137 and 139 in accordance with the switching state of the switching device 141. The resistances of the resistors 133, 137 and 139 are so selected that the analog signal fed to the pressure value correcter 135 with the switching device 141 open, i.e. blocking, represents the pressure in torrs and with the switching device 141 closed, i.e. conducting, represents the pressure in kilopascals. The control signal generator 143 then on each occasion also feeds to the analog-digital converter 145 a signal characterising the state of the switching device 141, so that the indicating unit 27 accordingly indicates the unit kilopascal or torr.

During the reading-out of the memories 63 and 65, i.e. during the indication of the systolic and diastolic pressures, the indicated value is corrected in dependence on the circumference of the arm of the person examined. For carrying out this correction, the measurement circuit 81 feeds to the correction value generator 83 an analog signal having a magnitude which represents the measured arm circumference U. In addition, the control unit 55 feeds a signal characterising these processes to the correction value generator 83 during the reading-out of the memory 63 or the memory 65. The correction value generator 83 includes means to generate an analog correction signal having a magnitude which is dependent on the one hand on the circumference of the arm and on the other hand on whether systolic or diastolic pressure is being read out. The pressure correcter 135 then corrects the analog signal, which is fed thereto by the impedance converter 131 and which represents the measured systolic or diastolic pressure, in accordance with the correction signal and feeds a corrected signal to the analog-digital converter 145.

It is pointed out that only the pressure signals read out of the memories 63 and 65 are corrected, and not those signals which give a measure of instantaneous pressure and are supplied at time intervals of, for example, 0.3 seconds during the course of the measurement. The signals representing measured heart frequency are fed directly from the control unit 55 to the analog-digital converter 145, i.e. bypassing the pressure value corrector 135, and are not, of course, subjected to any correction.

The influence of the circumference of the arm and the method of performing the pressure corrections will now be explained. The pressure-measuring channel is calibrated by means of a setting device (not shown) in such a manner that the correct pressure is indicated for a normal arm circumference, i.e. of average size. When the circumference of the arm is larger than normal, the pressure values determined without correction are greater than the actual pressure values. When the circumference of the arm increases by comparison with the width of the sleeve, the pressure generated by inflation of the sleeve is no longer completely transmitted through the body tissue to the artery. By contrast, when the circumference of the arm is below the normal size, the pressure values determined without correction are smaller than the actual pressure values.

In the following, the uncorrected pressure is generally indicated by p and the corrected pressure by p*. In addition, the uncorrected systolic and diastolic pressures are indicated by $p_S$ and $p_D$, respectively, and the corrected systolic and diastolic pressures by $p^*_S$ and $p^*_D$, respectively. As experimental examinations have shown, the connection between uncorrected and corrected pressure can be represented in a good approximation by the following general relationship:

$$p^* = p - k(U - a) \quad (3)$$

wherein U is again the circumference of the arm and a and k are constants. The constants a and k are somewhat different for the systolic pressure and the diastolic pressure. If the constants valid for correction of the systolic pressure are represented by $k_S$ and $a_S$ and the constants valid for correction of the diastolic pressure by $k_D$ and $a_D$, the following equations can be expressed:

$$p^*_S = p_S - k_S(U - a_S) \quad (4)$$

and $$p^*_D = p_D - k_D(U - a_D) \quad (5).$$

The values of the constants are dependent on the width and other constructional aspects of the sleeve 1. For a sleeve having a width of 12 centimeters, the following values were determined:

$a_S = 28$ centimeters; $k_S = 0.17$ kilopascals per centimeter, $a_D = 18$ centimeters; $k_D = 0.12$ kilopascals per centimeter.

The correction value generator 83 includes means to determine the circumference U according to the equations (1) and (2) on the basis of the measured capacitance at the transducer 43 and to then generate correction signals. These can be, for example, analog signals, i.e. voltages, which in the indication of the systolic pressure are proportional to the term $k_S(U - a_S)$ of the sum.

When the memory 63 is now read out for indication of the systolic pressure, the correction value generator 83 feeds the voltage proportional to the term $k_S(U - a_S)$ of the sum to the pressure value correcter 135. The pressure value correcter 135, which for example comprises an adding-subtracting circuit, then in accordance with the negative or positive value of the term $k_S(U - a_S)$ of the sum performs an addition or subtraction of the analog signals delivered by the impedance converter 131 and the correction generator 83, and provides at its output an analog signal, namely a voltage which is proportional to the true pressure $p^*_S$.

During the reading-out of the memory 65 and indication of the diastolic pressure, a correction according to the equation (5) is carried out in an analogous manner.

Figure 6:
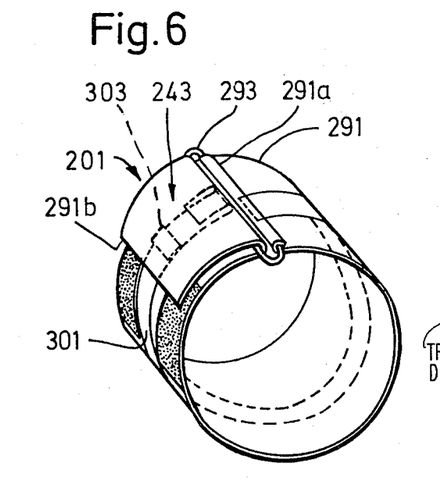
FIG. 6 is a perspective view of a sleeve, with a resistive measurement transducer, in a modification of the equipment of FIG. 1.

In FIG. 6, there is shown a sleeve 201, which is modified in relation to the sleeve 1 and which comprises a band 291, a buckle 293 and a resistive measurement transducer 243. The transducer 243 comprises a resistance track 301 of electrical resistance material, the track being elongate in the length direction of the band 291 and extending over at least a part of the length of the band. The track 301 is disposed on that side of the band which, in the portion of the band enclosing the arm, is remote from the arm. One end 291a of the band is fastened to the buckle 293, and its other end 291b is drawn, for attachment of the sleeve to an arm, through the buckle and folded over one of the buckle bars. A tap contact 303 is fastened to the band 291 in the region of the end 291b and is disposed on that side of the band which, after folding of that band end over the buckle bar, faces the resistance track 301. The end of the resistance track 301 at the band end 291a and the tap contact 303 are each connected with the conductor of the cable which connects the sleeve with the appliance 3.

Otherwise, the sleeve 201 is constructed in similar manner to the sleeve 1. When the sleeve 201 is attached to an arm, the tap contact 303 bears against the resistance track 301 at a place dependent on the circumference of the arm. The resistance measured between the connections of the measurement transducer 243 thus provides a measure of the circumference of the arm.

Figure 7:
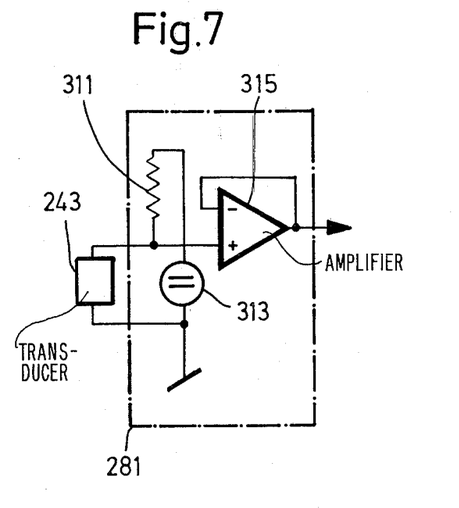
FIG. 7 is a circuit diagram of the resistive measurement transducer and associated measurement circuit.

The appliance with which the sleeve 201 is connected includes, amongst other things, a measurement circuit 281, the circuit diagram of which is shown in FIG. 7. The circuit 281 comprises a constant current source 313 of unidirectional current. One connection of the transducer 243 is connected with earth and with the earth connection of the constant current source 313. The other transducer connection is connected with the non-inverting input of an amplifier 315 provided with full feedback, and via a resistor 311 with that connection of the constant current source 313 which is not connected to earth.

The output of the amplifier 315 forms the output of the measurement circuit 281 and is connected with a correction value generator. This is constructed in such a manner that it can exercise a function corresponding to the correction value generator 83. The measurement circuit 281 and/or the correction value generator connected thereafter are provided with manually settable setting devices (not shown) for balancing and calibration of the circumference-measuring channel. The other pneumatic and electronic components of the appliance with which the sleeve 201 is connected are constructed in similar manner to those of the appliance 3.

A few further possible modifications of the blood pressure measuring equipment will now be mentioned.

Firstly, the low frequency generator 113, shown in FIG. 4 as a separate component, could be entirely or partly combined with a frequency generator necessary for the operation of the analog-digital converter 145.

In addition, the triangular electrode 103 of the capacitive measurement transducer 43 could be replaced by an electrode having a width which changes in the length direction of the band not linearly but in a different manner, this change in the width, however, preferably representing a progressive increase or decrease. A certain, non-linear relationship between arm circumference and measurement transducer capacitance can be achieved by such a construction of the measurement transducer electrode, and in some circumstances this may simplify the construction of the correction value generator and-/or pressure value correcter.

In analogous manner, in the case of the resistive measurement transducer 243 the width and/or thickness of the resistance track 301 could be varied along the sleeve.

According to the equations (3), (4) and (5), the correction of the pressure measurement values takes place by substraction of a correction value from the measurement values. The correction could, however, be carried out by other formulae of approximation. It would be possible, for example, to multiply the uncorrected pressure measurement values by a correction factor dependent on the circumference. In this case, the pressure value correcter 135 could comprise, instead of an addition-substraction circuit, a multiplication circuit for the multiplication of two magnitudes represented in analog manner. In this connection, it is also to be noted that the correction could be carried out not by use of equations but by storage of a number of correction values each allocated to a respective one of a plurality of stepped circumference measurements. The pressure values would then be corrected by one of the stored values in accordance with the arm circumference determined by the measurement transducer.

It is also pointed out that as the circumference of the arm is interlinked with the diameter of the arm, the pressure values could equally well be corrected in dependence on the diameter. A measurement transducer could be provided for direct measurement of the diameter. Such a measurement transducer could, for example, comprise an ultrasonic source and means for detection of the transit time of the ultrasonic waves.

In the embodiment of the blood pressure measuring equipment explained by reference to FIGS. 1 to 5, the pressure values are corrected on reading out of the memories 63 and 65. It would also be possible to correct the pressure values during the recording into the memories. In addition, the pressure values indicated at regular intervals during the blood pressure measurement could be corrected in dependence on the circumference of the arm. Moreover, the appliance could be equipped with a switch, by means of which it could be determined as desired whether or not the appliance should perform a pressure correction.

Finally, it is mentioned that the equipment could be adapted so that the sleeve is attachable not to an arm but to another member, for example a leg, of the person to be examined.

I claim:

1. Blood pressure measuring equipment comprising
a sleeve attachable to a limb of a person, said sleeve defining a chamber inflatable by fluid and being provided with a measurement transducer for measuring the circumference or diameter of a limb to which said sleeve is attached, said transducer comprising two electrodes so arranged on said sleeve as to provide, when said sleeve is attached to a limb, a capacitor having a capacitance dependent on the circumference of the limb,
a pressure sensor for detecting fluid pressure in said chamber, and
pressure value determining means electrically connected to said sensor to determine values of detected pressure levels in said chamber, said pressure value determining means comprising
pressure value correcting means connected to said transducer and adapted to correct at least some of said determined pressure values in dependence on the limb circumference or diameter measurement determined by said transducer.

2. Equipment according to claim 1, wherein one of said electrodes comprises a portion which extends along the sleeve in the circumferential direction thereof and varies in width along the sleeve in said direction, and the other one of said electrodes has a smaller dimension in said direction than said portion of said one electrode.

3. Equipment according to claim 1, further comprising storage means for storing electrical signals having magnitudes indicative of determined pressure values representing systolic and diastolic blood pressure measurements, indicating means responsive to said signals to provide indications of the associated values, and signal feed means for feeding said signals from said storage means to said indicating means, said pressure value correcting means being adapted to correct said values before or after storage of the respective signals in said storage means.

4. Equipment according to claim 1, wherein said pressure value determining means and said measurement transducer are adapted to provide electrical analog signals indicative of, respectively, said determined pressure values and said determined limb circumference or diameter measurement, and wherein said pressure value correcting means comprises means for logically combining in analog form said pressure value analog signals and said limb measurement analog signals.

5. Equipment according to claim 1, further comprising storage means for storing electrical analog signals indicative of said determined pressure values, indicating means connected to said storage means to receive said analog signals and provide indications of the associated values in a selectable one of at least two different measurement units, and circuit means selectably switchable into the connection between said storage means and said indicating means to so vary said analog signals as to effect a change in said indication of said values from one of said measurement units to the other of said measurement units.

6. A sphygmometer comprising:
a cuff wrappable about a limb and having end portions that overlap when wrapped around the limb, whereby the extent of overlap is proportional to the limb size;
respective electrodes on the overlapping portions of the cuff;
means for inflating the cuff, tightening same on the limb, and thereby juxtaposing the electrodes with each other, the electrodes forming a capacitor whose capacitance varies with limb size;

means for detecting fluid pressure in the cuff and for generating an output corresponding thereto;

circuit means connected to the electrodes for determining the capacitance therebetween and to the pressure-detecting means for modifying the output in accordance with limb size; and means for displaying the modified output.

7. The sphygmometer defined in claim 6 wherein one of the electrodes is formed as a flexible and elongated conductive tape of varying width.

8. The sphygmometer defined in claim 7 wherein the end portion of the cuff opposite the tape is provided with a buckle carrying the other electrode, the tape normally being looped through the buckle.

9. The sphygmometer defined in claim 8 wherein the cuff has a closure that secures the tape flatly and tightly over the buckle when the cuff is inflated.

* * * * *